United States Patent [19]

Thomas et al.

[11] Patent Number: 5,610,130

[45] Date of Patent: Mar. 11, 1997

[54] MICROEMULSION ALL-PURPOSE LIQUID CLEANING COMPOSITIONS WITH INSECT REPELLENT

[75] Inventors: Barbara J. Thomas, Princeton, N.J.; Myriam Loth, Saint-Nicolas, Belgium; Thomas F. Connors, Piscataway, N.J.; Myriam Mondin, Seraing, Belgium

[73] Assignee: Colgate-Palmolive Company, New York, N.Y.

[21] Appl. No.: 650,211

[22] Filed: May 20, 1996

Related U.S. Application Data

[63] Continuation of Ser. No. 381,606, Jan. 30, 1995, abandoned, which is a continuation-in-part of Ser. No. 228,538, Apr. 15, 1994, abandoned, which is a continuation-in-part of Ser. No. 155,317, Nov. 22, 1993, abandoned, which is a continuation-in-part of Ser. No. 102,314, Aug. 4, 1993, abandoned.

[51] Int. Cl.$^6$ .................. C11D 3/32; C11D 1/74; C11D 1/83; C11D 17/00

[52] U.S. Cl. .......... 510/383; 510/101; 510/365; 510/417; 510/422; 510/424; 510/437; 510/501; 510/505; 510/506

[58] Field of Search ................. 510/383, 417, 510/365, 422, 424, 437, 501, 505, 506 101

[56] References Cited

U.S. PATENT DOCUMENTS

| | | | |
|---|---|---|---|
| 3,466,246 | 9/1969 | Freugeau | 252/106 |
| 4,737,520 | 4/1988 | Naik et al. | 514/520 |
| 4,804,683 | 2/1989 | Steltenkamp | 514/629 |
| 5,006,562 | 4/1991 | Steltenkamp | 514/625 |
| 5,015,665 | 5/1991 | Steltenkamp | 514/625 |
| 5,075,026 | 12/1991 | Loth et al. | 252/122 |
| 5,076,954 | 12/1991 | Loth et al. | 252/122 |
| 5,082,584 | 1/1992 | Loth et al. | 252/122 |
| 5,091,111 | 2/1992 | Neumiller | 252/305 |
| 5,108,643 | 4/1992 | Loth et al. | 252/174.11 |
| 5,143,900 | 9/1992 | Steltenkamp et al. | 512/26 |
| 5,145,604 | 9/1992 | Neumiller | 252/312 |
| 5,182,304 | 1/1993 | Steltenkamp | 514/625 |
| 5,182,305 | 1/1993 | Steltenkamp | 514/629 |
| 5,258,408 | 11/1993 | Steltenkamp | 514/625 |
| 5,391,578 | 2/1995 | Steltenkamp | 514/625 |
| 5,403,509 | 4/1995 | Pujol et al. | 252/174.22 |

FOREIGN PATENT DOCUMENTS

| | | |
|---|---|---|
| 0316726 | 5/1989 | European Pat. Off. |
| 0525892 | 2/1993 | European Pat. Off. |
| 0525893 | 2/1993 | European Pat. Off. |
| 0619363 | 10/1994 | European Pat. Off. |
| 0637629 | 2/1995 | European Pat. Off. |
| 57-209999 | 12/1982 | Japan |
| 58-206693 | 12/1983 | Japan |
| 59-1600 | 1/1984 | Japan |

*Primary Examiner*—Ardith Hertzog
*Attorney, Agent, or Firm*—Bernard Lieberman; Henry S. Goldfine; James M. Serafino

[57] ABSTRACT

A stable oil-in-water microemulsion cleaning composition is provided which is essentially effective for the removal of oily and greasy soil from a hard surface and for repelling insects therefrom. The aqueous phase of said microemulsion comprises by weight of the total composition: (A) from about 0.1 to about 25% of a surfactant mixture of (i) an anionic surfactant; (ii) an ethoxylated glycerol-based nonionic surfactant mixture; the weight ratio of (i) and (ii) being from about 1:1 to about 5:1; and (iii) a salt of a multivalent metal cation in an amount sufficient to provide from 0.5 to 1.5 equivalents of cation per equivalent of (i); the anionic surfactant, the nonionic surfactant and amount of multivalent metal cation being selected so as to provide a cloud point of at least about 45° C. in the finished microemulsion composition; (B) from about 0.1% to about 30% of a water-soluble cosurfactant having substantially no ability to dissolve oily or greasy soil; and (C) the balance water. The oil phase of said microemulsion is comprised essentially of an effective amount of an insect repellent compound, and optionally a perfume or water insoluble hydrocarbon, said microemulsion composition being effective for removing oily and greasy soils from a hard surface and repelling insects therefrom by solubilizing such soils in the microemulsion while concomitantly depositing the insect repellent compound upon the hard surface to be cleaned to provide insect repelling properties thereto.

13 Claims, No Drawings

MICROEMULSION ALL-PURPOSE LIQUID CLEANING COMPOSITIONS WITH INSECT REPELLENT

This application is a continuation of U.S. Ser. No. 08/381,606, filed Jan. 30, 1995, now abandoned, which is a continuation-in-part of U.S. Ser. No. 8/228,538 filed Apr. 15, 1994, now abandoned, which is a continuation-in-part of U.S. Ser. No. 8/155,317 filed Nov. 22, 1993, now abandoned, which in turn is a continuation-in-part of U.S. Ser. No. 8/102,314 filed Aug. 4, 1993, now abandoned, the disclosures of which are incorporated herein by reference.

This invention relates to an improved all-purpose liquid cleaner in the form of a microemulsion designed in particular for cleaning hard surfaces and for imparting insect repelling properties to such hard surface. More particularly, this invention relates to liquid all purpose detergent compositions in microemulsion form which contain an insect repellent material and to a process for cleaning and repelling insects from surfaces and articles to which such microemulsion detergent compositions are applied.

BACKGROUND OF THE INVENTION

In recent years all-purpose liquid detergents have become widely accepted for cleaning hard surfaces, e.g., painted woodwork and panels, tiled walls, wash bowls, bathtubs, linoleum or tile floors, washable wall paper, etc.. Such all-purpose liquids comprise clear and opaque aqueous mixtures of water-soluble synthetic organic detergents and water-soluble detergent builder salts. In order to achieve comparable cleaning efficiency with granular or powdered all-purpose cleaning compositions, use of water-soluble inorganic phosphate builder salts was favored in the prior art all-purpose liquids. For example, such early phosphate-containing compositions are described in U.S. Pat. Nos. 2,560,839; 3,234,138; 3,350,319; and British Patent No. 1,223,739.

In view of the environmentalist's efforts to reduce phosphate levels in ground water, improved all-purpose liquids containing reduced concentrations of inorganic phosphate builder salts or non-phosphate builder salts have appeared. A particularly useful self-opacified liquid of the latter type is described in U.S. Pat. No. 4,244,840.

However, these prior art all-purpose liquid detergents containing detergent builder salts or other equivalent tend to leave films, spots or streaks on cleaned unrinsed surfaces, particularly shiny surfaces. Thus, such liquids require thorough rinsing of the cleaned surfaces which is a time-consuming chore for the user.

In order to overcome the foregoing disadvantage of the prior art all-purpose liquid, U.S. Pat. No. 4,017,409 teaches that a mixture of paraffin sulfonate and a reduced concentration of inorganic phosphate builder salt should be employed. On the other hand, another alternative to achieving phosphate-free all-purpose liquids has been to use a major proportion of a mixture of anionic and nonionic detergents with minor amounts of glycol ether solvent and organic amine as shown in U.S. Pat. No. 3,935,130. Again, this approach has not been completely satisfactory and the high levels of organic detergents necessary to achieve cleaning cause foaming which, in turn, leads to the need for thorough rinsing which has generally been found to be undesirable for today's consumers.

Another approach to formulating hard surface or all-purpose liquid detergent compositions where product homogeneity and clarity are important considerations involves the formation of oil-in-water (o/w) microemulsions which contain one or more surface-active detergent compounds, a water-immiscible solvent (typically a hydrocarbon solvent), water and a "cosurfactant" compound which provides product stability. By definition, an o/w microemulsion is a spontaneously forming colloidal dispersion of "oil" phase particles having a particle size in the range of about 25 to about 800 Å in a continuous aqueous phase. In view of the extremely fine particle size of the dispersed oil phase particles, microemulsions are transparent to light and are clear and usually highly stable against phase separation.

Patent disclosures relating to use of grease-removal solvents in o/w microemulsions include, for example, European Patent Applications EP 0137615 and EP 0137616—Herbots et al; European Patent Application EP 0160762—Johnston et al; and U.S. Pat. No. 4,561,991—Herbots et al. Each of these patent disclosures also teaches using at least 5% by weight of grease-removal solvent.

It also is known from British Patent Application GB 2144763A to Herbots et al, published Mar. 13, 1985, that magnesium salts enhance grease-removal performance of organic grease-removal solvents, such as the terpenes, in o/w microemulsion liquid detergent compositions. The compositions of this invention described by Herbots et al. require at least 5% of the mixture of grease-removal solvent and magnesium salt and preferably at least 5% of the solvent (which may be a mixture of water-immiscible non-polar solvent with a sparingly soluble slightly polar solvent) and at least 0.1% of the magnesium salt.

However, since the amount of water immiscible and sparingly soluble components which can be present in an o/w microemulsion, with low total active ingredients without impairing the stability of the microemulsion is rather limited (for example, up to about 18% by weight of the aqueous phase), the presence of such high quantities of grease-removal solvent tend to reduce the total amount of greasy or oily soils which can be taken up by and into the microemulsion without causing phase separation. The following representative prior art patents relate to liquid detergent cleaning compositions in the form of o/w microemulsions: U.S. Pat. Nos. 4,472,291—Rosario; 4,540,448—Gauteer et al; and 3,723,330—Sheflin.

U.S. Pat. Nos. 5,076,954, 5,075,026, 5,082,584 and 5,108,643, all in the name of Loth et al., describe liquid microemulsion compositions effective for removing grease soil and/or bath soil from hard surfaces. The described microemulsions contain specified combinations of anionic surfactant, nonionic surfactant, a cosurfactant, perfume and water.

Cleaning compositions for hard surfaces which have the capacity to clean as well as repel insects from the hard surface to which they are applied have been described in the art. European Patent Application 525 892 A1 to Steltenkamp et al. is directed to aqueous liquid detergent compositions for cleaning hard surfaces, which contain an insect repellent material such as those within the class of N-alkyl neoalkanamides wherein the alkyl is of 1 to 4 carbon atoms and the neoalkanoyl moiety is of 7 to 14 carbon atoms. However, heretofore insect repellents have never been used in conjunction with liquid microemulsion compositions which are capable of effectively cleaning a hard household surface, such as a kitchen wall, oven top, bathroom floor or the like with all the known attendant advantages of using a microemulsion, while at the same time applying a film of insect repellent material which is sufficiently substantive to the surface to which the composition is applied to repel insects therefrom.

SUMMARY OF THE INVENTION

The present invention provides a stable oil-in-water microemulsion cleaning composition which is especially effective for the removal of oily and greasy soil from a hard surface and for repelling insects therefrom, the aqueous phase of said microemulsion comprising by weight of the total composition:

(A) from about 0.1 to about 25% of a surfactant mixture of
  (i) an anionic surfactant;
  (ii) an ethoxylated glycerol-based nonionic surfactant mixture; the weight ratio of (i) to (ii) being from about 1:1 to about 5:1; and
  (iii) a salt of a multivalent metal cation in an amount sufficient to provide from 0.5 to 1.5 equivalents of cation per equivalent of (i); the anionic surfactant and amount of multivalent metal cation being selected so as to provide a cloud point of at least 45° C. in the finished microemulsion composition;

(B) from about 0 to about 5% of a fatty acid;

(C) from about 0.1% to about 30% of a water-soluble cosurfactant having substantially no ability to dissolve oily or greasy soil; and (D) the balance water;

the oil phase of said microemulsion being comprised essentially of an effective amount of an insect repellent material, and optionally a perfume or water insoluble hydrocarbon, said microemulsion composition being effective for removing oily and greasy soils from a hard surface and repelling insects therefrom by solubilizing such soils in the microemulsion while concomitantly depositing the insect repellent compound upon the hard surface to be cleaned to provide insect repelling properties thereto.

The dispersed oil phase of the microemulsion comprises from about 0.5 to about 20%, by weight, of the entire composition, preferably from about 2 to about 15%, by weight, and most preferably from about 2 to about 10%, by weight. Although, the microemulsion can be formed using the insect repelling material as the sole component in the oil phase, it is preferred to incorporate a minor amount of perfume to improve the consumer acceptability of the product.

The preferred insect repellent material useful for the present invention is a N-lower alkyl neoalkanamide having the structural formula

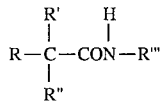

wherein the alkyl R''' is of 1 to 4 carbon atoms, preferably 1 to 2 carbon atoms, and the neoalkanoyl moiety

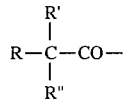

is of 7 to 14 carbon atoms, preferably neotridecanoyl and most preferably, neodecanoyl.

Methyl neodecanamide (MNDA) is the most preferred insect repellent material from among the neoalkanamides described above. A detailed description of the aforementioned neoalkanamides and their method of manufacture is found in numerous patents, such as, U.S. Pat. No. 5,258,408, the disclosure of which is incorporated herein by reference.

Other useful, albeit less preferred insect repellents may advantageously be used in the present compositions, most notably, N,N-diethyl-meta-toluamide having the commercial designation DEET.

The insect repelling material is generally present in the microemulsion cleaning composition in an amount of from about 0.5 to about 20%, by weight, of the composition, preferably from about 1 to about 8%, by weight, and most preferably from about 1 to about 5%, by weight, depending upon the desired level of insect repelling properties to be imparted to the hard surface contacted by the said microemulsion composition.

It is preferred that the microemulsion compositions of the invention are essentially free of an insecticide material, relying solely on the insect repellent material to impart repellent properties to the cleaned hard surface.

In accordance with the process aspect of the invention there is provided a process for cleaning a hard surface and repelling insects therefrom comprising applying to said hard surface the microemulsion cleaning composition as described above wherein the effective amount of insect repellent material is sufficient to repel insects from the hard surface after application of the microemulsion cleaning composition thereto.

The present invention is predicated on the discovery that an insect repelling material as used herein can be effectively solubilized in the oil phase of the defined microemulsion compositions to provide a liquid cleaning composition having the dual benefits of cleaning and being able to impart insect repelling properties to a cleaned surface. The microemulsion compositions are particularly advantageous in eliminating the need for a consumer to rinse the cleaned surface thereby allowing a more concentrated dosage of insect repellent to be applied to the hard surface.

Present commercial microemulsion cleaning compositions are generally too hydrophobic to incorporate within them an insect repellent material such as MNDA as manifested by the fact that upon addition of MDNA the resulting formulation has a cloud point of below 45° C. This is commercially unacceptable for the majority of consumer liquid cleaning products. The present invention provides microemulsions of sufficient hydrophilicity having cloud points of at least 45° C., preferably at least 50° C., and most preferably about 55° C.

The cloud point may be conveniently measured by the following technique:

5 ml test samples are equilibrated in a water bath at about 30° C. in 10 ml stoppered test tubes. The bath temperature is raised slowly, and the temperature at which each sample becomes cloudy is noted as the cloud point.

The microemulsions of the present invention which are designed to contain an insect repellent material as herein described are made more hydrophilic in order to provide the desired cloud point, principally, by adjusting the composition in one or more of the following ways:

(1) by lowering the amount of multivalent cation, typically magnesium ion, in the composition relative to the anionic surfactant;

(2) by selecting a more hydrophilic anionic surfactant; and (3) by utilizing a higher ratio of anionic surfactant to the ethoxylated glycerol-based nonionic surfactant mixture.

Alternatively, but less conveniently, a cosurfactant of increased hydrophilicity may be utilized. However, hydrophobic cosurfactants may be effectively utilized for the present microemulsion compositions provided the particular nonionic surfactant which is selected is sufficiently hydrophilic to provide the desired cloud point in the finished composition.

The microemulsion compositions of the present invention provide an improved, clear, liquid cleaning composition having improved interfacial tension which are suitable for cleaning hard surfaces such as plastic, vitreous and metal surfaces having a shiny finish. More particularly, the improved cleaning compositions exhibit good grease soil removal properties due to the improved interfacial tensions, when used in undiluted (neat) form and leave the cleaned surfaces shiny without the need of or requiring only minimal additional rinsing or wiping. The latter characteristic is evidenced by little or no visible residues on the unrinsed cleaned surfaces and, accordingly, overcomes one of the disadvantages of prior art products. Surprisingly, these desirable results are accomplished even in the absence of polyphosphate or other inorganic or organic detergent builder salts and also in the complete absence or substantially complete absence of grease-removal solvent.

The microemulsion compositions can be provided in the form of substantially dilute oil-in-water microemulsions wherein the aqueous phase, and oil phase have compositions as described above. Alternatively, in accordance with a second aspect of the invention there is provided highly concentrated microemulsion compositions in the form of either an oil-in-water (o/w) microemulsion or a water-in-oil (w/o) microemulsion which when diluted with additional water before use forms a dilute o/w microemulsion composition. The dilute and concentrated microemulsion compositions generally contain, by weight, from about 0.1 to 20%, of an anionic surfactant; from about 0.1 to 20% of an ethoxylated glycerol-based nonionic surfactant mixture; from about 0 to 5% of a fatty acid; from about 0.4 to 10% of perfume; from about 0.5 to 20% of an insect repellent material; from about 0.1 to 30% of a cosurfactant; and from about 20 to 97% of water as the balance of the composition. The mixture of anionic and ethoxylated glycerol-based nonionic surfactant mixtures is generally from about 0.1 to 25% with the weight ratio of anionic to ethoxylated glycerol-based nonionic surfactant mixture being from about 1:1 to 5:1.

DETAILED DESCRIPTION OF THE INVENTION

The present invention relates to stable microemulsion compositions in diluted or concentrated form having the compositions as described above.

According to the present invention, the role of the hydrocarbon to form the oil phase is provided by the insect repellent material as well as by the water-insoluble perfume. Typically, in aqueous based compositions the presence of solubilizers, such as alkali metal lower alkyl aryl sulfonate hydrotrope, triethanolamine, urea, etc., is required for perfume dissolution, especially at perfume levels of about 1% and higher, since perfumes are generally a mixture of fragrant essential oils and aromatic compounds which are generally not water-soluble. Therefore, by incorporating the perfume into the aqueous cleaning composition as the oil (hydrocarbon) phase of the ultimate o/w microemulsion composition in conjunction with the insect repellent material, several different important advantages are achieved.

First, the cosmetic properties of the ultimate cleaning composition are improved: the compositions are both clear (as a consequence of the formation of a microemulsion) and highly fragranced (as a consequence of the perfume level).

Second, the need for use of solubilizers, which do not contribute to cleaning performance, is eliminated.

Third, an improved grease removal capacity in neat (undiluted) usage of the dilute aspect or after dilution of the concentrate can be obtained without detergent builders or buffers or conventional grease removal solvents at neutral or acidic pH and at low levels of active ingredients while improved cleaning performance can also be achieved in diluted usage.

As used herein and in the appended claims the term "perfume" is used in its ordinary sense to refer to and include any water-insoluble fragrant substance or mixture of substances including natural (i.e., obtained by extraction of flower, herb, blossom or plant), and artificial (i.e., mixture of natural oils or oil constituents and synthetically produced substances) odoriferous substances. Typically, perfumes are complex mixtures of blends of various organic compounds such as alcohols, aldehydes, ethers, aromatic compounds and varying amounts of essential oils (e.g., terpenes) such as from about 0% to about 80%, usually from about 10% to 70% by weight, the essential oils themselves being volatile odoriferous compounds and also serving to dissolve the other components of the perfume.

In the present invention the precise composition of the perfume is of no particular consequence to cleaning performance so long as it meets the criteria of water immiscibility and having a pleasing odor. Naturally, of course, especially for cleaning compositions intended for use in the home, the perfume, as well as all other ingredients, should be cosmetically acceptable, i.e., non-toxic, hypoallergenic, etc.

The hydrocarbon such as a perfume is present in the dilute o/w microemulsion in an amount of from about 0.4% to about 10% by weight, preferably from about 0.4% to about 3.0% by weight, especially preferably from about 0.5% to about 2.0% by weight. If the amount of hydrocarbon, whether derived from the insect repellent material or from perfume is less than about 0.4% by weight it becomes difficult to form the o/w microemulsion.

Furthermore, although superior grease removal performance will be achieved for perfume compositions not containing any terpene solvents, it is apparently difficult for perfumers to formulate sufficiently inexpensive perfume compositions for products of this type (i.e., very cost sensitive consumer-type products) which include less than about 20%, usually less than about 30%, of such terpene solvents.

Thus, merely as a practical matter, based on economic consideration, the dilute o/w microemulsion detergent cleaning compositions of the present invention may often include as much as about 0.2% to about 7% by weight, based on the total composition, of terpene solvents introduced thereunto via the perfume component. However, even when the amount of terpene solvent in the cleaning formulation is less than 1.5% by weight, such as up to about 0.6% by weight or 0.4% by weight or less, satisfactory grease removal and oil removal capacity is provided by the inventive diluted o/w microemulsions.

Regarding the anionic detergent present in the o/w microemulsions any of the conventionally used water-soluble anionic detergents or mixtures of said anionic detergents and nonionic detergents can be used in this invention. As used herein the term "anionic surfactant" is intended to refer to the class of anionic and mixed anionic-nonionic detergents providing detersive action.

The water-soluble organic detergent materials which are used in forming the ultimate o/w microemulsion compositions of this invention may be selected from the group consisting of water-soluble, non-soap, anionic detergents mixed with a fatty acid and a nonionic detergents.

Suitable water-soluble non-soap, anionic detergents include those surface-active or detergent compounds which contain an organic hydrophobic group containing generally 8 to 26 carbon atoms and preferably 10 to 18 carbon atoms in their molecular structure and at least one water-solubilizing group selected from the group of sulfonate, sulfate and carboxylate so as to form a water-soluble detergent. Usually, the hydrophobic group will include or comprise a $C_8-C_{22}$ alkyl, alkenyl or acyl group. Such detergents are employed in the form of water-soluble salts and the salt-forming cation usually is selected from the group consisting of sodium, potassium, ammonium, magnesium and mono-, di- or tri-$C_2-C_3$ alkanolammonium, with the sodium, magnesium and ammonium cations again being preferred.

Examples of suitable sulfonated anionic detergents are the well known higher alkyl mononuclear aromatic sulfonates such as the higher alkyl benzene sulfonates containing from 10 to 16 carbon atoms in the higher alkyl group in a straight or branched chain, $C_8-C_{15}$ alkyl toluene sulfonates and $C_8-C_{15}$ alkyl phenol sulfonates.

A preferred sulfonate is linear alkyl benzene sulfonate having a high content of 3-(or higher) phenyl isomers and a correspondingly low content (well below 50%) of 2-(or lower) phenyl isomers, that is, wherein the benzene ring is preferably attached in large part at the 3 or higher (for example, 4, 5, 6 or 7) position of the alkyl group and the content of the isomers in which the benzene ring is attached in the 2 or 1 position is correspondingly low. Particularly preferred materials are set forth in U.S. Pat. No. 3,320,174.

Other suitable anionic detergents are the olefin sulfonates, including long-chain alkene sulfonates, long-chain hydroxyalkane sulfonates or mixtures of alkene sulfonates and hydroxyalkane sulfonates. These olefin sulfonate detergents may be prepared in a known manner by the reaction of sulfur trioxide ($SO_3$) with long-chain olefins containing 8 to 25, preferably 12 to 21 carbon atoms and having the formula $RCH=CHR_1$ where R is a higher alkyl group of 6 to 23 carbons and $R_1$ is an alkyl group of 1 to 17 carbons or hydrogen to form a mixture of sultones and alkene sulfonic acids which is then treated to convert the sultones to sulfonates. Preferred olefin sulfonates contain from 14 to 16 carbon atoms in the R alkyl group and are obtained by sulfonating an alpha-olefin.

Other examples of suitable anionic sulfonate detergents are the paraffin sulfonates containing about 10 to 20, preferably about 13 to 17, carbon atoms. Primary paraffin sulfonates are made by reacting long-chain alpha olefins and bisulfites and paraffin sulfonates having the sulfonate group distributed along the paraffin chain are shown in U.S. Pat. Nos. 2,503,280; 2,507,088; 3,260,744; 3,372,188; and German Patent 735,096.

Examples of satisfactory anionic sulfate detergents are the $C_8-C_{18}$ alkyl sulfate salts and the $C_8-C_{18}$ alkyl ether polyethenoxy sulfate salts having the formula $R(OC_2H_4)n$ $OSO_3M$ wherein n is 1 to 12, preferably 1 to 5, and M is a solubilizing cation selected from the group consisting of sodium, potassium, ammonium, magnesium and mono-, di- and triethanol ammonium ions. The alkyl sulfates may be obtained by sulfating the alcohols obtained by reducing glycerides of coconut oil or tallow or mixtures thereof and neutralizing the resultant product. On the other hand, the alkyl ether polyethenoxy sulfates are obtained by sulfating the condensation product of ethylene oxide with a $C_8-C_{18}$ alkanol and neutralizing the resultant product. The alkyl ether polyethenoxy sulfates differ from one another in the number of moles of ethylene oxide reacted with one mole of alkanol. Preferred alkyl sulfates and preferred alkyl ether polyethenoxy sulfates contain 10 to 16 carbon atoms in the alkyl group.

The $C_8-C_{12}$ alkylphenyl ether polyethenoxy sulfates containing from 2 to 6 moles of ethylene oxide in the molecule also are suitable for use in the inventive compositions. These detergents can be prepared by reacting an alkyl phenol with 2 to 6 moles of ethylene oxide and sulfating and neutralizing the resultant ethoxylated alkylphenol.

Other suitable anionic detergents are the $C_5-C_{15}$ alkyl ether polyethenoxyl carboxylates having the structural formula $R(OC_2H_4)_nOXCOOH$ wherein n is a number from 4 to 12, preferably 5 to 10 and X is selected from the group consisting of $CH_2(C(O)R_1)$ and $C(O)$, wherein $R_1$, is a $C_1-C_3$ alkylene group. Preferred compounds include $C_9-C_{11}$ alkyl ether polyethenoxy (7–9) $C(O)$ $CH_2CH_2COOH$, $C_{13}-C_{15}$ alkyl ether oxide with the appropriate alkanol and reacting this reaction product with chloracetic acid to make the ether carboxylic acids as shown in U.S. Pat. No. 3,741,911 or with succinic anhydride or phthalic anhydride. Obviously these anionic detergents will be present either in acid form or salt form depending upon the pH of the final composition, with salt forming cation being the same as for the other anionic detergents.

Of the foregoing non-soap anionic detergents, the preferred detergents are the $C_9-C_{15}$ linear alkylbenzene sulfonates and the $C_{13}-C_{17}$ paraffin or alkane sulfonates. Particularly, preferred compounds are sodium $C_{10}-C_{13}$ alkylbenzene sulfonate and sodium $C_{13}-C_{17}$ alkane sulfonate.

Generally, the proportion of the nonsoap-anionic detergent will be in the range of 0.1% to 20.0%, preferably from 1% to 7%, by weight of the dilute o/w microemulsion composition.

The ethoxylated glycerol-based nonionic surfactant mixture which is a mixture of a fully esterified ethoxylated polyhydric alcohol, a partially esterified ethoxylated polyhydric alcohol and a nonesterified ethoxylated polyhydric alcohol, wherein the preferred polyhydric alcohol is glycerol, and the compound is:

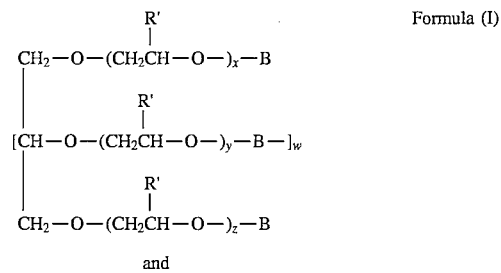

Formula (I)

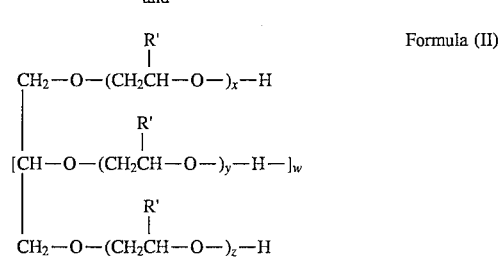

Formula (II)

wherein w equals one to four, most preferably one. B is selected from the group consisting of hydrogen or a group represented by:

wherein R is selected from the group consisting of alkyl group having about 6 to 22 carbon atoms, more preferably about 11 to about 15 carbon atoms and alkenyl groups having about 6 to 22 carbon atoms, more preferably about 11 to 15 carbon atoms, wherein a hydrogenated tallow alkyl chain or a coco alkyl chain is most preferred, wherein at least one of the B groups is represented by said

and R' is selected from the group consisting of hydrogen and methyl groups; x, y and z have a value between 0 and 60, more preferably 0 to 40, provided that (x+y+z) equals about 2 to about 100, preferably 4 to about 24 and most preferably about 4 to 19, wherein in Formula (I) the ratio of monoester/diester/triester is 45 to 90/5 to 40/1 to 20, more preferably 50 to 90/9 to 32/1 to 12, wherein the ratio of Formula (I) to Formula (II) is a value between about 3 to about 0.02, preferably 3 to about 0.1, most preferably about 1.5 to about 0.2, wherein it is most preferred that there is more of Formula (II) than Formula (I) in the mixture that forms the compound.

The ethoxylated glycerol-based nonionic surfactant mixture used in the instant composition is manufactured by the Kao Corporation and sold under the trade name Levenol such as Levenol F-200 which has an average EO of 6 and a molar ratio of coco fatty acid to glycerol of 0.55 or Levenol V501/2 which has an average EO of 17 and a molar ratio of tallow fatty acid to glycerol of 1.0. It is preferred that the molar ratio of the fatty acid to glycerol is less than about 1.7, more preferably less than about 1.5 and most preferably less than about 1.0. The ethoxylated glycerol-based nonionic surfactant mixture has a molecular weight of about 400 to about 1600, and a pH (50 grams/liter of water) of about 5–7. The Levenol compounds are substantially non irritant to human skin and have a primary biodegradabillity higher than 90% as measured by the Wickbold method Bias-7d.

Two examples of the Levenol compounds are Levenol V-501/2 which has 17 ethoxylated groups and is derived from tallow fatty acid with a fatty acid to glycerol ratio of 1.0 and a molecular weight of about 1465 and Levenol F-200 has 6 ethoxylated groups and is derived from coco fatty acid with a fatty acid to glycerol ratio of 0.55. Both Levenol F-200 and Levenol V-501/2 are composed of a mixture of Formula (I) and Formula (II). The Levenol compounds has ecoxicity values of algae growth inhibition>100 mg/liter; acute toxicity for Daphniae>100 mg/liter and acute fish toxicity>100 mg/liter. The Levenol compounds have a ready biodegradability higher than 60% which is the minimum required value according to OECD 301B measurement to be acceptably biodegradable.

Polyesterified nonionic compounds also useful in the instant compositions are Crovol PK-40 and Crovol PK-70 manufactured by Croda GMBH of the Netherlands. Crovol PK-40 is a polyoxyethylene (12) Palm Kernel Glyceride which has 12 EO groups. Crovol PK-70 which is prefered is a polyoxyethylene (45) Palm Kernel Glyceride have 45 EO groups.

In the preferred dilute o/w microemulsion compositions the proportion of ethoxylated glycerol-based nonionic surfactant mixtures based upon the weight of the final dilute o/w microemulsion composition will be 0.1% to 10.0%, more preferably 0.5% to 5%, by weight. Furthermore, in the more preferred compositions the weight ratio of nonsoap anionic detergent to the ethoxylated glycerol-based nonionic surfactant mixture will be in the range of 1:1 to 5:1 with especially good results being obtained at a weight ratio of 1:1 to 2:1.

The cosurfactant may play an essential role in the formation of the dilute o/w microemulsion and the concentrated microemulsion compositions. Very briefly, in the absence of the cosurfactant the water, detergent(s) and hydrocarbon (e.g., perfume or insect repellent material) will, when mixed in appropriate proportions form either a micellar solution (low concentration) or form an oil-in-water emulsion in the first aspect of the invention. With the cosurfactant added to this system, the interfacial tension at the interface between the emulsion droplets and aqueous phase is reduced to a very low value. This reduction of the interfacial tension results in spontaneous break-up of the emulsion droplets to consecutively smaller aggregates until the state of a transparent colloidal sized emulsion. e.g., a microemulsion, is formed. In the state of a microemulsion, thermodynamic factors come into balance with varying degrees of stability related to the total free energy of the microemulsion. Some of the thermodynamic factors involved in determining the total free energy of the system are (1) particle-particle potential; (2) interfacial tension or free energy (stretching and bending); (3) droplet dispersion entropy; and (4) chemical potential changes upon formation. A thermodynamically stable system is achieved when (2) interfacial tension or free energy is minimized and (3) droplet dispersion entropy is maximized. Thus, the role of cosurfactant in formation of a stable o/w microemulsion is to (a) decrease interfacial tension (2); and (b) modify the microemulsion structure and increase the number of possible configurations (3). Also, the cosurfactant will (c) decrease the rigidity.

Four major classes of compounds have been found to provide highly suitable cosurfactants over temperature ranges extending from 5° C. to 43° C. for instance; (1) water-soluble $C_3$–$C_4$ alkanols, polypropylene glycol of the formula $HO(CH_3CHCH_2O)_n H$ wherein n is a number from 2 to 18 and monoalkyl ethers and esters of ethylene glycol and propylene glycol having the structural formulas $R(X)_n OH$ and $R_1(X)_n OH$ wherein R is $C_1$–$C_9$ alkyl, $R_1$ is $C_1$–$C_4$ acyl group, X is $(OCH_2CH_2)$ or $(OCH_3CHCH_2)$ and n is a number from 1 to 4; (2) aliphatic mono-and di-carboxylic acids containing 3 to 6 carbons in the molecule; (3) the aforementioned alkyl ether polyethenoxy carboxylic acids discussed above when the anionic carboxylate form of this compound is not present; and (4) triethyl phosphate. Additionally, mixtures of two or more of the four classes of cosurfactant compounds may be employed where specific pH's are desired.

Representative members of the polypropylene glycols include dipropylene glycol and polypropylene glycol having a molecular weight of 200 to 1000, e.g., polypropylene glycol 400. Other satisfactory glycol ethers are ethylene glycol monobutyl ether (butyl cellosolve), diethylene glycol monobutyl ether (butyl carbitol), triethylene glycol monobutyl ether, mono, di, tri propylene glycol monobutyl ether, tetraethylene glycol monobutyl ether, propylene glycol tertiary butyl ether, ethylene glycol monoacetate and dipropylene glycol propionate.

Still other classes of cosurfactant compounds providing stable microemulsion compositions at low and elevated temperatures are the aforementioned alkyl ether polyethenoxy carboxylic acids and the mono-, di- and triethyl esters of phosphoric acid such as triethyl phosphate.

The amount of cosurfactant required to stabilize the microemulsion compositions will, of course, depend on such factors as the surface tension characteristics of the cosurfactant, the type and amounts of the primary surfactants and perfumes, and the type and amounts of any other additional ingredients which may be present in the composition and which have an influence on the thermodynamic factors enumerated above. Generally, amounts of cosurfactant in the range of from 0% to 30%, preferably from about 0.5% to 15%, especially preferably from about 1% to 7%, by weight provide stable dilute o/w microemulsions for the above-described levels of primary surfactants and perfume and any other additional ingredients as described below.

As will be appreciated by the practitioner, the pH of the final microemulsion will be dependent upon the identity of the cosurfactant compound, with the choice of the cosurfactant being effected by cost and cosmetic properties, particularly odor. For example, microemulsion compositions which have a pH in the range of 1 to 10 may employ either the class 1 or the class 4 cosurfactant as the sole cosurfactant, but the pH range is reduced to 1 to 8.5 when the polyvalent metal salt is present. The class 2 cosurfactant can only be used as the sole cosurfactant when the product pH is below 3.2. Similarly, the class 3 cosurfactant can be used as the sole cosurfactant where the product pH is below 5. However, where the acidic cosurfactants are employed in admixture with a glycol ether cosurfactant, compositions can be formulated at substantially neutral pH.

The final essential ingredient in the inventive microemulsion compositions having improved interfacial tension properties is water. The proportion of water in the microemulsion compositions generally is in the range of 20% to 97%, preferably 70% to 97% by weight of the usual diluted o/w microemulsion composition.

As previously described, the dilute o/w microemulsion liquid all-purpose cleaning compositions of this invention are especially effective when used as is, that is, without further dilution in water, since the properties of the composition as an o/w microemulsion are best manifested in the neat (undiluted) form. However, at the same time it should be understood that depending on the levels of surfactants, cosurfactants, perfume and other ingredients, some degree of dilution without disrupting the microemulsion, per se, is possible. For example, at the preferred low levels of active surfactant compounds (i.e., primary anionic and nonionic detergents) dilutions up to about 50% will generally be well tolerated without causing phase separation, that is, the microemulsion state will be maintained.

However, even when diluted to a great extent, such as a 2- to 10-fold or more dilution, for example, the resulting compositions are still effective in cleaning greasy, oily and other types of soil. Furthermore, the presence of magnesium ions or other polyvalent ions, e.g., aluminum, as will be described in greater detail below further serves to boost cleaning performance of the primary detergents in dilute usage.

On the other hand, it is also within the scope of this invention to formulate highly concentrated microemulsions which will be diluted with additional water before use.

The present invention also relates to a stable concentrated microemulsion composition comprising approximately by weight:

(a) 0.1 to 20% of an anionic surfactant;
(b) 0.1 to 20% of an ethoxylated glycerol-based nonionic surfactant mixture; the mixture of anionic and nonionic surfactants being generally from about 0.1 to 25%;
(c) 0 to 5% of a fatty acid;
(d) 0.1 to 30% of a cosurfactant;
(e) 0.5 to 20% of an insect repellent material, e.g. MNDA;
(f) 0.4 to 10% of a water insoluble hydrocarbon or perfume;
(g) 0 to 18% of at least one mono or dicarboxylic acid;
(h) 0 to 15% of magnesium sulfate heptahydrate; and
(i) balance being water.

Such concentrated microemulsions can be diluted by mixing with up to about 20 times or more, preferably about 4 to about 10 times their weight of water to form o/w microemulsions similar to the diluted microemulsion compositions described above. While the degree of dilution is suitably chosen to yield an o/w microemulsion composition after dilution, it should be recognized that during the course of dilution both microemulsion and non-microemulsions may be successively encountered.

In addition to the above-described essential ingredients required for the formation of the microemulsion composition, the compositions of this invention may often and preferably do contain one or more additional ingredients which serve to improve overall product performance.

One such ingredient is an inorganic or organic salt or oxide of a multivalent metal cation, particularly $Mg^{++}$. The metal salt or oxide provides several benefits including improved cleaning performance in dilute usage, particularly in soft water areas, and minimized amounts of perfume required to obtain the microemulsion state. Magnesium sulfate, either anhydrous or hydrated (e.g., heptahydrate), is especially preferred as the magnesium salt. Good results also have been obtained with magnesium oxide, magnesium chloride, magnesium acetate, magnesium propionate and magnesium hydroxide. These magnesium salts can be used with formulations at neutral or acidic pH since magnesium hydroxide will not precipitate at these pH levels.

Although magnesium is the preferred multivalent metal from which the salts (inclusive of the oxide and hydroxide) are formed, other polyvalent metal ions also can be used provided that their salts are nontoxic and are soluble in the aqueous phase of the system at the desired pH level. Thus, depending on such factors as the pH of the system, the nature of the primary surfactants and cosurfactant, and so on, as well as the availability and cost factors, other suitable polyvalent metal ions include aluminum, copper, nickel, iron, calcium, etc. It should be noted, for example, that with the preferred paraffin sulfonate anionic detergent calcium salts will precipitate and should not be used. It has also been found that the aluminum salts work best at pH below 5 or when a low level, for example about 1 weight percent, of citric acid is added to the composition which is designed to have a neutral pH. Alternatively, the aluminum salt can be directly added as the citrate in such case. As the salt, the same general classes of anions as mentioned for the magnesium salts can be used, such as halide (e.g., bromide, chloride), sulfate, nitrate, hydroxide, oxide, acetate, propionate, etc.

Preferably, in the dilute compositions the metal compound is added to the composition in an amount sufficient to provide at least a stoichiometric equivalence between the anionic surfactant and the multivalent metal cation. For example, for each gram-ion of $Mg^{++}$ there will be 2 gram moles of paraffin sulfonate, alkylbenzene sulfonate, etc., while for each gram-ion of $Al^{3+}$ there will be 3 gram moles of anionic surfactant. Thus, the proportion of the multivalent salt generally will be selected so that one equivalent of compound will neutralize from 0.5 to 1.5 equivalents, preferably 0.9 to 1.1 equivalents, of the acid form of the anionic detergent. At higher concentrations of anionic detergent, the amount of multivalent salt will be in range of 0.5 to 1.5 equivalents per equivalent of anionic detergent, preferably a range of about 0.8 to 1.2, equivalents of multivalent salt to equivalent of anionic.

The o/w microemulsion compositions will include from 0% to 5%, preferably from 0.1% to 2.0% by weight of the composition of a $C_8$–$C_{22}$ fatty acid or fatty acid soap as a foam suppressant. The addition of fatty acid or fatty acid soap provides an improvement in the rinseability of the composition whether applied in neat or diluted form. Generally, however, it is necessary to increase the level of cosurfactant to maintain product stability when the fatty acid or soap is present.

As example of the fatty acids which can be used as such or in the form of soap, mention can be made of distilled coconut oil fatty acids, "mixed vegetable" type fatty acids (e.g. high percent of saturated, mono-and/or polyunsaturated $C_{18}$ chains); oleic acid, stearic acid, palmitic acid, eiocosanoic acid, and the like, generally those fatty acids having from 8 to 22 carbon atoms being acceptable.

The all-purpose liquid cleaning composition of this invention may, if desired, also contain other components either to provide additional effect or to make the product more attractive to the consumer. The following are mentioned by way of example: Colors or dyes in amounts up to 0.5% by weight; bactericides in amounts up to 1% by weight; preservatives or antioxidizing agents, such as formalin, 5-bromo-5-nitro-dioxan-1,3; 5-chloro-2-methyl-4-isothaliazolin-3-one, 2,6-di-tert.butyl-p-cresol, etc., in amounts up to 2% by weight; and pH adjusting agents, such as sulfuric acid or sodium hydroxide, as needed. Furthermore, if opaque compositions are desired, up to 4% by weight of an opacifier may be added.

In final form, the all-purpose liquids are clear oil-in-water microemulsions and exhibit stability at reduced and increased temperatures. More specifically, such compositions remain clear and stable in the range of 5° C. to 50° C., especially 10° C. to 43° C. Such compositions exhibit a pH in the acid or neutral range depending on intended end use. The liquids are readily pourable and exhibit a viscosity in the range of 6 to 60 milliPascal.second (mPas.) as measured at 25° C. with a Brookfield RVT Viscometer using a #1 spindle rotating at 20 RPM. Preferably, the viscosity is maintained in the range of 10 to 40 mPas.

The compositions are directly ready for use or can be diluted as desired and in either case no or only minimal rinsing is required and substantially no residue or streaks are left behind. Furthermore, because the compositions are free of detergent builders such as alkali metal polyphosphates they are environmentally acceptable and provide a better "shine" on cleaned hard surfaces.

When intended for use in the neat form, the liquid compositions can be packaged under pressure in an aerosol container or in a pump-type or trigger sprayer for the so-called spray-and-wipe type of application.

Because the compositions as prepared are aqueous liquid formulations and since no particular mixing is required to form the o/w microemulsion, the compositions are easily prepared simply by combining all the ingredients in a suitable vessel or container. The order of mixing the ingredients is not particularly important and generally the various ingredients can be added sequentially or all at once or in the form of aqueous solutions of each or all of the primary detergents and cosurfactants can be separately prepared and combined with each other and with the perfume. The magnesium salt, or other multivalent metal compound, when present, can be added as an aqueous solution thereof or can be added directly. It is not necessary to use elevated temperatures in the formation step and room temperature is sufficient.

The following examples illustrate the microemulsion liquid cleaning compositions of the described invention. Unless otherwise specified, all percentages are by weight. The exemplified compositions are illustrative only and do not limit the scope of the invention.

EXAMPLE 1

The following insect repellent microemulsion formulations were prepared.

| | Weight Percent | | | |
|---|---|---|---|---|
| Material | A | B | C | D |
| Deionized Water | 89.65 | 89.9 | 89.3 | 89.3 |
| Paraffin Sulfonate | 2.0 | 2.0 | 2.0 | 2.0 |
| Levenol F200 | 2.0 | 2.0 | 2.0 | 2.0 |
| $MgSO_4 7H_2O$ | 0.75 | 0.5 | 0.5 | 0.5 |
| DEGMBE[1] | 2.8 | 2.8 | 2.8 | 2.8 |
| MNDA[2] | 2.0 | 2.0 | 2.0 | 0.0 |
| DEET[2] | 0.0 | 0.0 | 0.0 | 2.0 |
| Perfume | 0.8 | 0.8 | 0.8 | 0.8 |
| Coco Fatty Acid | 0.0 | 0.0 | 0.5 | 0.5 |
| Color | 0.0 | 0.0 | 0.12 | 0.12 |
| pH | 6.5 | 6.5 | 6.5 | 6.5 |
| Cloud Point °C. | 65 | >70 | >70 | >70 |

[1] Diethylene glycol monobutyl ether
[2] Insect repellent materials described hereinabove All of the above formulations provided an acceptable cloud point. Cleaning tests were performed comparing the grease cleaning effects of Composition C in accordance with the invention and Composition E is a commercial microemulsion cleaning composition having the following approximate composition:

| Material | Weight Percent E |
|---|---|
| C14–17 Paraffin Sulfonate | 4.0 |
| Ethoxylated Alcohol | 2.5 |
| Magnesium Sulfate Heptahydrate | 1–2 |
| Diethylene Glycol Monobutyl ether | 2.8 |
| pH | 6.5 |
| Water | Balance |

Composition C in accordance with the invention provided good grease cleaning when used at full strength and when diluted. It was comparable in performance to the commercial formulation E when used at the same dilution.

EXAMPLE 2

Composition E of Example 1, a commercial microemulsion composition not in accordance with the invention was used as the base composition to which was added 2%, by weight, of MNDA repellent. The resultant formula had a cloud point of about 38° C. and manifested separation of the formula into distinct phases at temperatures above 38° C. The compositions of the invention, by comparison, are characterized by cloud points above about 45° C.

We claim:

1. A stable oil-in-water microemulsion cleaning composition which is especially effective for the removal of oily and greasy soil from a hard surface and for repelling insects therefrom, the aqueous phase of said microemulsion comprising by weight of the total composition:

(A) from about 0.1% to about 25% of a surfactant mixture of
  (i) an anionic surfactant;
  (ii) an ethoxylated glycerol-based nonionic surfactant mixture; the weight ratio of (i) to (ii) being from about 1:1 to about 5:1; and
  (iii) a salt of a multivalent metal cation in an amount sufficient to provide from 0.5 to 1.5 equivalents of cation per equivalent of (i); the anionic surfactant and amount of multivalent metal cation being selected so as to provide a cloud point of at least about 45° C. in the finished microemulsion composition;

(B) from about 0 to 5% of a fatty acid;

(C) from about 0.1% to about 30% of a water-soluble cosurfactant having substantially no ability to dissolve oily or greasy soil, and wherein said cosurfactant is different from (i) and (ii); and (D) the balance water;

the oil phase of said microemulsion being comprised essentially of an effective amount of an insect repellent compound, and optionally a perfume or water insoluble hydrocarbon, said microemulsion composition being effective for removing oily and greasy soils from a hard surface and repelling insects therefrom by solubilizing such soils in the microemulsion while concomitantly depositing the insect repellent compound upon the hard surface to be cleaned to provide insect repelling properties thereto.

2. A cleaning composition as in claim 1 wherein the cosurfactant is selected from the group consisting of (a) water-soluble $C_3$–$C_4$ alkanols, (b) polypropylene glycol, (c) $C_1$–$C_9$ alkyl ethers, (d) $C_1$–$C_4$ alkyl esters of ethylene glycol, (e) $C_1$–$C_4$ alkyl esters of propylene glycol, (f) aliphatic mono-and di- carboxylic acids containing 3 to 6 carbons in the molecule, (g) $C_9$–$C_{15}$ alkyl ether polyethenoxy carboxylic acids of the structural formula $R(OC_2H_4)_nOXCOOH$ wherein R is $C_9$–$C_{15}$ alkyl, n is a number form 4 to 12 and X is selected from the group consisting of $CH_2$, and $C(O)R_1$, wherein $R_1$ is a $C_1$–$C_3$ alkylene group, and (h) mono-, di- and triethyl phosphate.

3. A cleaning composition as in claim 1, wherein the multivalent metal cation is selected from the group consisting of magnesium and aluminum.

4. A cleaning composition as in claim 3 wherein the salt of magnesium is selected from the group consisting of magnesium oxide, magnesium chloride and magnesium sulfate.

5. A cleaning composition as in claim 4 wherein the salt of magnesium is present in an amount to provide from about 0.8 to 1.2 equivalents of cation per equivalent of anionic surfactant.

6. A cleaning composition as in claim 1 wherein said anionic surfactant is paraffin sulfonate.

7. A cleaning composition as in claim 1 wherein the insect repellent is a N-alkyl neoalkanamide wherein the alkyl is of 1 to 2 carbon atoms and the neoalkanoyl moiety is of 7 to 14 carbon atoms.

8. A cleaning composition as in claim 7 wherein the insect repellent material is methyl neodecanamide.

9. A cleaning composition as in claim 1 wherein said insect repellent is N,N Diethyl Toluamide (DEET).

10. A process for cleaning a hard surface and for repelling insects therefrom comprising applying to said hard surface a microemulsion cleaning composition as described in claim 1.

11. A process according to claim 10 wherein said insect repellent material is methyl neodecanamide.

12. A process according to claim 10 wherein the multivalent metal cation is selected from the group consisting of magnesium and aluminum.

13. A process according to claim 12 wherein the salt of magnesium or aluminum is present in an amount to provide from about 0.8 to 1.2 equivalents of cation per equivalent of anionic surfactant.

* * * * *